USO05759544A

United States Patent [19]
Harada

[11] Patent Number: 5,759,544
[45] Date of Patent: Jun. 2, 1998

[54] ANTIBODY-CONTAINING ORAL COMPOSITION FOR SUPPRESSION OF PERIODONTAL DISEASE

[75] Inventor: Yoshihiro Harada, Odawara, Japan

[73] Assignee: Lion Corporation, Tokyo, Japan

[21] Appl. No.: 498,109

[22] Filed: Jul. 5, 1995

Related U.S. Application Data

[63] Continuation of Ser. No. 95,418, Jul. 22, 1993, abandoned.

[30] Foreign Application Priority Data

| Jul. 23, 1992 | [JP] | Japan | 4-217153 |
| Jul. 23, 1992 | [JP] | Japan | 4-217154 |
| Jul. 23, 1992 | [JP] | Japan | 4-217156 |

[51] Int. Cl.$^6$ .................. A61K 6/097; A61K 39/395; A61K 39/40; C07K 16/12
[52] U.S. Cl. .................. 424/137.1; 424/130.1; 424/150.1; 424/164.1; 530/389.1; 530/389.5; 530/387.5; 530/388.4; 514/900; 514/902
[58] Field of Search .................. 530/389.1, 889.5, 530/387.5, 388.4, 389.5; 514/900, 901, 902; 424/130.1, 137.1, 150.1, 164.1, 165.1, 175.1

[56] References Cited

U.S. PATENT DOCUMENTS

| 4,328,313 | 5/1982 | Simonson et al. | 435/200 |
| 4,430,322 | 2/1984 | Stoudt et al. | 435/97 |
| 4,689,221 | 8/1987 | Kiyoshige et al. | 530/389.5 |
| 4,933,182 | 6/1990 | Higashi et al. | 424/435 |

FOREIGN PATENT DOCUMENTS

| 60-142915 | 7/1985 | Japan . |
| 60-146834 | 8/1985 | Japan . |
| 1313438 | 12/1989 | Japan . |
| 253716 | 2/1990 | Japan . |

OTHER PUBLICATIONS

Place, Deborah et al. Inf & Immun. 56(5): 1394–1398, May 1988.
Sevier et al., Clinical Chemistry, vol. 27, No. 11, pp. 1797–1806 (1981).
Robins, Immunology in Plant Sciences, Linskens et al. (Eds), Springer–Verlag, New York, pp. 86–141 (1986).
Goodman, Basic & Clinical Immunology, Fudenberg et al. (ed.), Lange Medical Publications, Los Altos, pp. 32–40, (1976).
Bach et al., Immunology Today, vol. 14, No. 9, pp. 421–425 (1993).
Wilson et al., Infection and Immunity, vol. 59, No. 4, pp. 1544–1551 (1991).
Califano et al., Infection and Immunity, vol. 57, No. 5, pp. 1582–1589 (1989).

*Primary Examiner*—Susan A. Loring
*Attorney, Agent, or Firm*—Birch, Stewart, Kolasch & Birch, LLP

[57] ABSTRACT

An oral composition comprises an effective amount of an antibody obtained by immunizing an animal with an antigen comprised of at least one polysaccharide derived from the surface layer of periodontal disease associated bacteria. The at least one polysaccharide may be conjugated with polypeptides to further enhance the efficacy.

19 Claims, No Drawings

ANTIBODY-CONTAINING ORAL COMPOSITION FOR SUPPRESSION OF PERIODONTAL DISEASE

This application is a continuation, of application Ser. No. 08/095,418 filed on Jul. 22, 1993, now abandoned.

BACKGROUND OF THE INVENTION

1. Field of the Invention

This invention relates to oral compositions which can suppress periodontal disease associated bacteria such as *Actinobacillus actinomycetemcomitans*, *Porphyromonas gingivalis* and the like, from colonization to oral surfaces thereby preventing or curing the periodontal disease.

2. Description of the Prior Art

For the prevention of periodontal diseases, it is effective to inhibit virulence-associated bacteria from colonization on oral surfaces, thereby suppressing their propagation. From this point of view, there have been heretofore proposed oral compositions or anti-periodontal compositions wherein antibodies for the periodontal disease associated bacteria are formulated (Japanese Laid-Open Patent Application Nos. 60-142915 and 1-313438). However, these are antibodies prepared from an immunogen made of entire bodies of bacteria, or mixtures such as extracts of bacteria, so that interaction with other types of strains would not be negated. In addition, such compositions are not satisfactory with respect to the actual efficacy.

Accordingly, there is a demand or developing effective ingredients which can conveniently suppress colonization of periodontal disease associated bacteria on oral surfaces thereby effectively preventing the periodontal diseases.

Especially, although *Actinobacillus actinomycetemcomitans* has been considered to be the most potential bacterium for juvenile periodontitis, such bacteria have recently been frequently detected and isolated from the periodontal pocket of adult periodontic patients. Thus, greater attention has been paid to the bacteria as taking part in occurrence and development of periodontal diseases.

It has been already known that the antibody obtained by immunization of mammals or domestic fowls with the whole bacteria or a bacterial component of *Actinobacillus actinomycetemcomitans* is formulated in oral compositions to suppress colonization of the bacteria on oral surfaces, thereby preventing the oral diseases (Japanese Laid-Open Patent Application Nos. 60-146834 and 2-53716).

In general, however, where the whole bacteria or a fraction containing a plurality of proteins is used as an antigen, there arises the problem on the uniformity and safety of the resultant antibody. Additionally, if a specific type of protein of the bacteria is provided as an antigen, much labor is required for the preparation of an antigen, presenting the problem on the productivity. This is far away from a level of practical application.

SUMMARY OF THE INVENTION

It is an object of the present invention to provide an oral composition which can suppress colonization of periodontal disease associated bacteria on oral surfaces to prevent or cure the periodontal diseases.

In order to achieve the above object, we made intensive studies on bacteria of periodontal diseases. As a result, it was found that when polysaccharides derived from the surface layer of the virulence-associated bacteria were prepared and used as an antigen to immunize animals such as mammals or domestic fowls therewith, or preferably when polysaccharides derived from the surface layer of the periodontophatic bacteria were prepared and provided as an antigen after conjugation or coupling with polypeptides for immunization of the animal, the resultant antibody in blood, antibody in milk or antibody in egg remarkably suppressed colonization of the bacteria on oral surfaces. Thus, if these antibodies are formulated in oral compositions, the periodontal disease can be effectively prevented or cured.

Especially, it was found that when polysaccharides of the following formulas (a), (b) and (c) derived from the surface layer of bacteria of *Actinobacillus actinomycetemcomitans* were provided to immunize animals such as mammals or domestic fowls with any of the polysaccharides alone or in combination with polypeptides for use as an antigen, the resultant antibody in blood, antibody in milk or antibody in egg could remarkably suppress colonization of *Actinobacillus actinomycetemcomitans* on oral surfaces. Thus when these antibodies are formulated in an oral composition, the periodontal disease can be effectively prevented or cured.

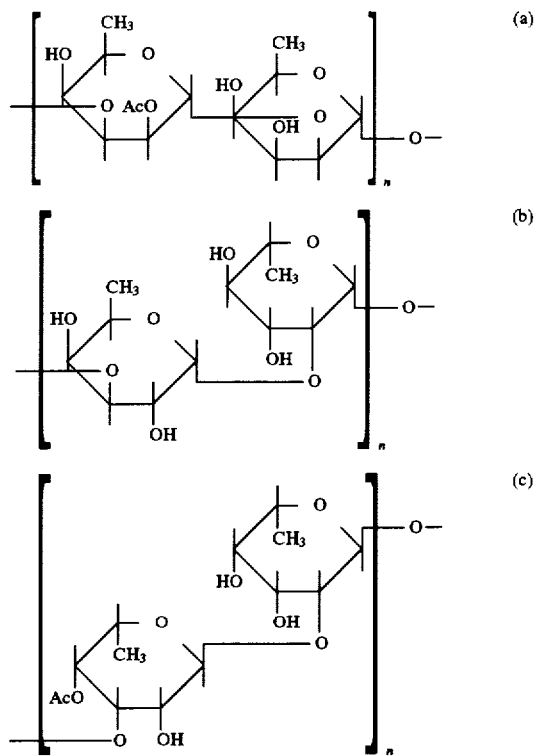

where Ac represents an acetyl group and n is an integer of 1 or over.

According to one embodiment of the invention, there is provided an oral composition which comprises an effective amount of an antibody obtained by immunizing an animal with an antigen comprised of at least one polysaccharide derived from the surface layer of periodontal disease associated bacteria.

According to another embodiment of the invention, there is also provided an oral composition which comprises an effective amount of an antibody obtained by immunizing an animal with an antigen comprised of at least one polysaccharide derived from the surface layer of periodontal disease associated bacteria and conjugated with a polypeptide.

According to a further embodiment of the invention, there is provided an oral composition which comprises an antibody obtained by immunizing an animal with an antigen comprised of at least one polysaccharide selected from polysaccharides of the general formulas (a), (b) and (c) indicated above or the at least one polysaccharide conjugated or joined with a polypeptide.

DETAILED DESCRIPTION OF THE INVENTION

The antigen used for obtaining the antibody which is formulated in the oral composition of the present invention consists of at least one polysaccharide derived from the surface layer of periodontal disease associated bacteria.

The periodontal disease associated bacteria are ones which are generally considered as having a close etiological relation with the periodontal diseases and include, for example, Actinobacillus actinomycetemcomitans, Porphyromonas gingivalis, Prevotella intermedia, Fusobacterium nucleatum, species of Capnocytophaga, Eikenella corrodens, Wolinella recta, Baceteroides forsythus, spirochetes such as Treponema denticola and the like.

The polysaccharides derived from the surface layer of these periodontopathic bacteria can be prepared by any known procedure. For instance, there may be utilized a process wherein cultivated bacteria are treated in an autoclave, a process wherein nitrites are reacted with the bacteria to extract, and a process where the bacteria are subjected to phenol/water extraction.

The antigen which is preferably used is at least one polysaccharide of the following formula (a), (b) or (c).

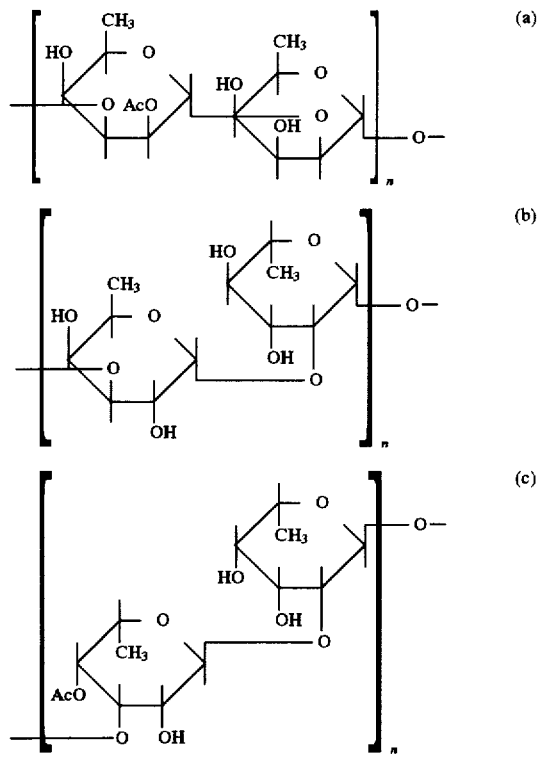

In the above formulas, Ac represents an acetyl group and n is an integer of 1 or over, preferably an integer of from 10 to 1000.

Although the antigen of the compound (a), (b) or (c) may be one which is chemically prepared from monosaccharides or which is prepared according to carbohydrate chain engineering techniques, it is preferred to use a serotype specific polysaccharide antigen obtained by extraction and purification from the bacterium Actinobacillus actinomycetemcomitans.

The above compounds (a), (b) and (c) can be, respectively, prepared from bacteria of serotypes a, b and c of Actinobacillus actinomycetemcomitans. In this case, the strain of the serotype a may be Actinobacillus actinomycetemcomitans ATCC 29523, SUNYaB75 or the like. Likewise, the strain of the serotype b may be ATCC 43718 (Y4), ATCC 29522 or the like. The strain of serotype c may be NCTC 9710, SUNYaB67 or the like.

In the practice of the invention, it is more preferred to use an antigen which consists of polysaccharides derived from the surface layer of the periodontopathic bacteria or polysaccharides (a), (b) and (c), to which polypeptides are conjugated.

The polypeptides conjugated to the polysaccharides derived from the surface layer of the bacteria are not critical and should preferably be those polypeptides which are inexpensive and which can remarkably increase the antibody titer relative to polysaccharides when conjugated with a polysaccharide to provide an immunogen. The polypeptides used for this purpose include various albumins such as BSA (bovine serum albumin), ovalbumin and the like, γ-globulin, casein, biotin, choleratoxin B sub-unit, ferritin, transferrin, cytochrome C, myosin and the like.

The conjugation between the surface layer polysaccharide and the polypeptide may be conducted by ordinary methods of coupling between polysaccharides and polypeptides provided that such methods enable polysaccharides and polypeptides to be coupled without changing the antigenicity of the polysaccharide used. More particularly, both an adsorption method and a covalent coupling method may be used, of which the covalent coupling method is preferred in view of the intensity of the binding force. A number of procedures for the covalent coupling of polysaccharides with polypeptides are known in the art. Any known procedures may be used in the practice of the invention. For instance, such procedures include a procedure wherein the polysaccharide is activated with cyanogen bromide, after which a polypeptide is joined, a procedure wherein an aromatic amino group is introduced into the polysaccharide, followed by diazo coupling with the aromatic group of a polypeptide, a procedure wherein an amino group is introduced into the polysaccharide, followed by reaction with the amino group of a polypeptide to form a Schiff's base, and a procedure wherein after reaction between the polysaccharide and a tresyl chloride, the resultant polysaccharide is coupled with the amino group or thiol group of a polypeptide.

For the immunization of animals with the antigen, there may be used subcutaneous injection, intramuscular injection, oral injection, intravenous injection, pernasal administration, peroral administration, peroral mucosal administration and the like. In order to increase the antibody titer, there can be conveniently used the immunization method using adjuvants such as Freund's incomplete and complete adjuvants, chorelatoxin B sub-unit and the like. The animals to be immunized include mammals such as rabbit, goat, sheep, cow, horse and the like, and fowls such as chicken, wild duck, ostrich, domestic duck, coturnix quail and the like. The antigens used for the immunization may be used singly or in combination.

The oral composition of the invention comprises an antibody in blood or in milk which is obtained by immunizing a mammal with the antigen defined above or an antibody in egg which is obtained by immunizing a fowl. For this purpose, the antiserum, milk or egg containing such an antibody as set out above may be formulated as it is. Alternatively, according to ordinary purification procedures, the antibody may be purified from the antiserum, milk or egg to formulate such a purified antibody in the oral composition. The antibody used in the invention can be purified from the serum, milk or egg by any known ordinary method. Such purification methods include, for example, salting-out, gel filtration, ion exchange chromatography, affinity chromatography and the like.

In the oral composition of the invention, the antibodies may be used on their own or in combination. The dose of the antibody is preferably in the range of 0.0001 to 50 mg/kg-day. The antibody is present in the composition in an amount of from 0.0002 to 10 wt % (hereinafter referred to simply as %), preferably from 0.002 to 5%.

The oral composition of the invention may be used in the form of dentifrices such as toothpastes, toothpowders, liquid dentifrices and the like, liquid refrigerants such as mouth washes, troches, oral pastes, massage creams for gingiva, gargles, chewing gums, candy, dairy products, and the like. Other additives of the oral composition of the invention may depend on the types of oral compositions.

With toothpastes, for example, there may be used abrasives such as calcium hydrogenphosphate, calcium carbonate, calcium pyrophosphate, insoluble sodium metaphosphate, amorphous silica, crystalline silica, aluminosilicate, aluminium oxide, aluminium hydroxide, resins and the like (in an amount of 10 to 95% by weight in general, binders such as carboxy-methylcellulose, hydroxyethyl cellulose, aluginates, carrageenan, gum arabic, polyvinyl alcohol and the like (in an amount of 0.1 to 10% by weight in general), humectants such as polyethylene glycol, sorbitol, glycerine, propylene glycol and the like (in an amount of 5 to 70% by weight in general), foaming agents such as sodium laurylsulfate, sodium dodecylbenzenesulfonate, hydrogenated coconut fatty acid monoglyceride, sodium monosulfate, sodium laurylsulfoacetate, sodium N-lauroylsarcosinate, N-acylglutaminates, sucrose fatty acid esters and the like (in an amount of 0.1 to 10% by weight in general), essential oils such as peppermint oil, spearmint oil and the like, flavors such as 1-menthol, carvone, eugenol, anethole and the like, sweetening agents such as sodium saccharin, stevioside, neohesperidyldihydrochalcone, glycyrrhizin, perillartine, p-methoxysinnamic aldehyde and the like, and preservatives. These additives are mixed in the conventional blending amounts with water to prepare the toothpaste by a usual manner. With other oral compositions such as mouth washes, appropriate additives may be added depending on the required properties of the product.

In the practice of the invention, other effective ingredients such as dextranase, mutanase, sorbic acid, chlorhexidine, hinokitiol, cetylpyridinium chloride, alkylglycines, alkyl diaminoethylglycine salts, allantoin, ε-aminocaproic acid, tranexamic acid, azulene, vitamin E, water soluble mono or dibasic phosphates, quaternary ammonium compounds, sodium chloride, crude drug extracts and the like may be blended into the oral composition.

The oral composition of the present invention is formulated with antibodies obtained by immunizing animals with a specific type of antigen, so that periodontal disease associated bacteria are appropriately suppressed from colonization on oral surfaces thereby effectively preventing or curing the disease. The antibody has high specificity against the bacteria for the periodontal disease and can be obtained at high productivity.

The present invention is more particularly described by way of examples.

EXPERIMENTAL EXAMPLE 1

(1) Preparation of polysaccharides from the surface layer of bacteria

*Actinobacillus actinomycetemcomitans* Y4 (ATCC 43718) was inoculated in TODD-HEWITT broth supplemented with 1% yeast extract, and cultured in an incubator containing 5% $CO_2$ at 37° C. for 3 days. After collection of the resultant bacteria, they were washed with saline three times and then suspended in saline, followed by autoclaving at 121° C. for 15 minutes. After cooling, the suspension was centrifuged at 10,000×g for 20 minutes, and the supernatant was collected. Saline was again added to the settled residue, followed by repeating the above extraction. The supernatants were combined together, dialyzed extensively against distilled water, and lyophilized to obtain a polysaccharide derived from the surface layer of bacteria.

The general procedure set out above was repeated except that the strain of Porphyromonas gingivalis 381 (FERM BP-1027) was cultivated in TODD-HEWITT broth supplemented with hemin and menadione for 2 days and the resultant bacteria were collected, thereby obtaining a surface layer polysaccharide.

(2) Coupling between the surface layer polysaccharide and a polypeptide

Each surface layer polysaccharide thus obtained was activated with cyanogen bromide, followed by reaction with dihydrazide adipate to introduce the amino group. Then, bovine serum albumin (BSA) was coupled to the polysaccharide according to the carbodiimide method. This surface layer polysaccharide-BSA was provided as an immunogen.

(3) Preparation of antibody

The thus prepared antigen was used for immunization of rabbits to obtain an antibody. The immunization was conducted according to an ordinary procedure. More particularly, an initial immunization was effected by subcutaneous injection of 1 mg of the polysaccharide antigen along with Freund's complete adjuvant. Thereafter, 2 mg of the polysaccharide antigen was intravenously administered at the ear four times in total every seven days. The resultant antiserum was subjected to salting out twice with a 50% saturated of ammonium sulfate solution, followed by dialysis against saline to obtain an antibody specimen.

(4) Assessment of antibody (i) Bacteria-agglutinating activity of the surface layer polysaccharide immunized rabbit serum antibody The agglutinating activity of these antibody specimens on bacteria was determined.

*Actinobacillus actinomycetemcomitans* Y4 (ATCC 43718), Porphyromonas gingivalis 381 (FERM BP-1027), *Streptococcus sanguis* ATCC 15560, and *Streptococcus salivarius* ATCC 13419 were, respectively, cultivated to the late stage of a logarithmic propagation phase. After collection of the resultant bacteria for each strain, the bacteria were washed three times with saline and then suspended in saline at $OD_{550nm}=1.0$. On the other hand, the respective antibody specimens were placed in saline to have a protein concentration of 1 mg/ml, thereby providing antibody assay samples for the bacteria-agglutinating activity. The respective assay samples were each subjected to doubling dilutions with saline. The bacteria suspension was added to each dilution in an amount equal to that of the dilution, followed by agitation and allowing to stand overnight. Thereafter, the agglutination of the bacteria was visibly observed. The results are shown in Table 1.

TABLE 1

| Type of antibody (Immunogen) | Agglutinating activity for the strains indicated below* | | | |
|---|---|---|---|---|
| | A. actinomycetemcomitans Y4 | P. gingivalis 381 | S. sanguis ATCC 10556 | S. salivarius ATCC 13419 |
| non-immune antibody (adjuvant alone) | 4 | 4 | 4 | 4 |
| anti-A.a.Y4 antibody (whole cells of Y4) | 256 | 32 | 16 | 32 |
| anti-P.g.381 antibody (whole cells of 381) | 32 | 512 | 32 | 32 |
| anti-Y4 surface layer polysaccharide antibody (Y4 surface layer polysaccharide) | 128 | 4 | 4 | 4 |
| anti-381 surface layer polysaccharide antibody (381 surface layer polysaccharide) | 4 | 256 | 4 | 4 |
| anti-Y4 surface layer polysaccharide-BSA (Y4 surface layer polysaccharide - BSA) | 1024 | 4 | 4 | 4 |
| anti-381 surface layer polysaccharide-BSA antibody (381 surface layer polysaccharide - BSA) | 4 | 2048 | 4 | 4 |

The agglutinating activity is indicated by a maximum dilution of the respective antibody assay sample (1 mg of protein/ml).

The results of Table 1 reveal that the antibodies obtained by immunization of the bacterial surface layer polysaccharide used as an antigen exhibit low reactivity with indigenous bacteria in the oral cavity such as Streptococcus sanguis, Streptococcus salivarius and the like and have thus high specificity. In comparison with the case where the surface layer polysaccharide is used as an antigen for the immunization, it will be seen that the antibodies obtained by using the polysaccharide-BSA antigens for the immunization exhibit remarkably higher reactivity with the bacteria.

(ii) Effect of Inhibiting Colonization of

Actinobacillus actinomycetemcomitans in Oral Cavity of Hamster by Means of Antibodies from Y4 Bacterial Surface Layer Polysaccharide Immunized Rabbit Serum Actinobacillus actinomycetemcomitans Y4 (ATCC 43718) which had been cultivated for 3 days was suspended in a 1 mM phosphate buffer at $OD_{550nm}=1.0$. The suspension was mixed with the respective antibodies at a ratio by volume of 1:1, followed by reaction at 37° C. for 30 minutes. For control, the suspension was mixed with a phosphate buffer instead of the antibody solution.

The respective mixtures were each inoculated to groups of hamsters, each consisting of eight hamsters, in an amount of 0.1 ml per day over successive five days. One week after completion of the inoculation, the marginal portion of the gingivae of each hamster was swabbed with a sterilized cotton swab to count the bacteria of Actinobacillus actinomycetemcomitans and all bacteria. The ratio of the bacteria of Actinobacillus actinomycetemcomitans to all the bacteria is calculated and is provided as a rate of Actinobacillus actinomycetemcomitans. The results are shown in Table 2.

TABLE 2

| | Ratio (%) of Actinobacillus actinomycetemcomitans |
|---|---|
| Phosphate buffer | 2.95 ± 0.94 ] * |
| Anti-Y4 surface layer polysaccharide antibody | 1.16 ± 0.64 ] ] ** |
| Anti-Y4 surface layer polysaccharide - BSA antibody | 0.42 ± 0.19 ] * |

*: $P < 0.05$
**: $P < 0.01$

As will be apparent from Table 2, the anti-Y4 surface layer polysaccharide antibody which is an antibody of the invention can inhibit the colonization, on oral surfaces, of the Actinobacillus actinomycetemcomitans in significance upon comparison with the control. Moreover, the anti-Y4 surface layer polysaccharide-BSA antibody of the invention can significantly inhibit the colonization of Actinobacillus actinomycetemcomitans when compared with the anti-Y4 surface layer polysaccharide antibody, with the inhibiting effect being more pronounced on comparison with the control.

(iii) Effect of Inhibiting Colonization of Porphyromonas gingivalis in Oral Cavity of Hamster by Means of Antibodies from 381 Bacterial Surface Layer Polysaccharide Immunized Rabbit Serum Porphyromonas gingivalis 381 (FERM BP-1027) which had been cultivated for 3 days was suspended in a 1 mM phosphate buffer at $OD_{550nm}=1.0$. The suspension was mixed with an anti-381 surface layer polysaccharide antibody or an anti-381 surface layer polysaccharide-BSA antibody at a ratio by volume of 1:1, followed by reaction at 37° C. for 30 minutes. For control, the suspension was mixed with a phosphate buffer instead of the antibody solution.

Groups of hamsters, each consisting of eight hamsters, were each ligated with a cotton thread at the first molar tooth of the lower jaw, after which each mixture was applied to the hamsters in an amount of 0.1 ml per day over successive five days. One week after completion of the inoculation, the ligated thread was removed to count the bacteria of *Porphyromonas gingivalis* and the total number of anaerobic bacteria in the thread. The ratio of the bacteria of *Porphyromonas gingivalis* to the total number of anaerobic bacteria is calculated and is provided as a rate of the *Porphyromonas gingivalis*. The results are shown in Table 3.

TABLE 3

| | Ratio (%) of *Porphyromonas gingivalis* |
|---|---|
| Phosphate buffer | 4.79 ± 1.05 |
| Anti-381 surface layer polysaccharide antibody | 1.13 ± 0.54 |
| Anti-381 surface layer polysaccharide - BSA antibody | 0.49 ± 0.23 |

\*: $P < 0.05$
\*\*: $P < 0.01$

As will be apparent from Table 3, the anti-381 surface layer polysaccharide antibody which is an antibody of the invention can significantly inhibit the colonization, on oral surfaces, of *Porphyromonas gingivalis* upon comparison with the control. Moreover, the anti-381 surface layer polysaccharide-BSA antibody of the invention has a significantly high effect of inhibiting the colonization of *Porphyromonas gingivalis* when compared with the anti-381 surface layer polysaccharide antibody, with the inhibiting effect being more pronounced on comparison with the control.

EXPERIMENTAL EXAMPLE 2
(1) Preparation of Polysaccharide Antigen

The strains of *Actinobacillus actinomycetemcomitans* (ATCC 29523, Y4 (ATCC 43718) and NCTC 9710) were each inoculated in TODD-HEWITT broth supplemented with 1% yeast extract, and cultured in an incubator containing 5% $CO_2$ at 37° C. for 3 days. After collection of the resultant bacteria, they were washed with saline three times and then suspended in saline, followed by autoclaving at 121° C. for 15 minutes. After cooling, the suspension was centrifuged at 10,000×g for 20 minutes, and the supernatant was collected. Saline was again added to the settled residue, followed by repeating the above extraction. The supernatants were combined together, dialyzed extensively against distilled water, and lyophilized. The resultant specimen was dissolved in a 0.01M tris-hydrochloride buffer (pH 8.2) at a concentration of 100 mg/ml, followed by dialysis against the buffer at 4° C. for two days. The resultant solution was subjected to ion exchange chromatography using a DEAE-SEPHADEX A-25 column equilibrated with the buffer used above. Sugar peak fractions which passed through without adsorption were collected and concentrated in a rotary evaporator, followed by dialysis against distilled water to a satisfactory extent. The resultant dialyzate was subjected to gel filtration using SEPHACRYL S-300 column. A single sugar peak fraction was collected and lyophilized to obtain a polysaccharide antigen.

(2) Coupling between the polysaccharide antigen and a polypeptide

The thus obtained polysaccharide antigen was activated with cyanogen bromide, followed by reaction with dihydrazide adipate to introduce the amino group. Then, bovine serum albumin (BSA) was coupled to the polysaccharide antigen according to the carbodiimide method. This provided a polysaccharide-BSA antigen.

(3) Preparation of antibody

The thus prepared polysaccharide antigen or polysaccharide-BSA antigen was used for immunization of rabbits to obtain an antibody. The immunization was conducted according to an ordinary procedure. More particularly, an initial immunization was effected by subcutaneous injection of 1 mg of the polysaccharide antigen along with Freund's complete adjuvant. Thereafter, 2 mg of the polysaccharide antigen was intravenously administered at the ear four times in total every seven days. The resultant antiserum was subjected to salting out twice with a 50% saturated of ammonium sulfate solution, followed by dialysis against saline to obtain an antibody specimen.

(4) Effect of Inhibiting Colonization of *Actinobacillus actinomycetemcomitans* in Oral Cavity of Hamster by Means of Rabbit Serum Antibodies Strains of *Actinobacillus actinomycetemcomitans* which had been cultivated for 3 days were suspended in a 1 mM phosphate buffer at $OD_{550nm}=1.0$. The suspension was mixed with the respective antibody at a ratio by volume of 1:1, followed by reaction at 37° C. for 30 minutes. For control, the suspension was mixed with a phosphate buffer instead of the antibody solution.

The respective mixtures were each inoculated into groups of hamsters, each consisting of eight hamsters, in an amount of 0.1 ml per day over successive five days. One week after completion of the inoculation, the marginal portion of the gingivae of each hamster was swabbed with a sterilized cotton swab to count the bacteria of *Actinobacillus actinomycetemcomitans* and all the bacteria. The ratio of the bacteria of *Actinobacillus actinomycetemcomitans* to all the bacteria is calculated and is provided as a rate of *Actinobacillus actinomycetemcomitans*. The above procedure was repeated, three times in total, using different types of strains being immunized (Experiments A, B and C). The results are shown in Tables 4 to 6.

TABLE 4

Experiment A
(inoculated strain: ATCC 29523)

| | Ratio (%) of *Actinobacillus actinomycetemcomitans* |
|---|---|
| Phosphate buffer | 2.72 ± 0.78 |
| Anti-polysaccharide (a) antibody | 1.13 ± 0.52 |
| Anti-polysaccharide (a) - BSA antibody | 0.54 ± 0.22 |

\*: $P < 0.05$
\*\*: $P < 0.01$

TABLE 5

Experiment B
(inoculated strain: Y4)

| | Ratio (%) of *Actinobacillus actinomycetemcomitans* |
|---|---|
| Phosphate buffer | 2.95 ± 0.94 |
| Anti-polysaccharide (b) antibody | 1.20 ± 0.59 |

TABLE 5-continued

Experiment B
(inoculated strain: Y4)

| | Ratio (%) of Actinobacillus actinomycetemcomitans | |
|---|---|---|
| Anti-polysaccharide (b) - BSA antibody | 0.48 ± 0.25 | * |

*: P < 0.05
**: P < 0.01

TABLE 6

Experiment C
(inoculated strain: NCT 9710)

| | Ratio (%) of Actinobacillus actinomycetemcomitans | | |
|---|---|---|---|
| Phosphate buffer | 2.66 ± 0.97 | * | |
| Anti-polysaccharide (c) antibody | 1.29 ± 0.61 | | ** |
| Anti-polysaccharide (c) - BSA antibody | 0.51 ± 0.20 | * | |

*: P < 0.05
**: P < 0.01

As will be apparent from Tables 4 to 6, the respective antibodies can significantly inhibit the colonization of, on oral surfaces, of Actinobacillus actinomycetemcomitans when compared with the control group. In addition, when the BSA-conjugated polysaccharides are used as the antigen, there was a more pronounced effect in inhibiting the colonization than that of the case using the polysaccharides alone.

The present invention is described by way of examples in which percent is by weight. In the examples, indicated by A.a. is Actinobacillus actinomycetemcomitans, by P.g. is Pophyromonas gingivalis, by P.i. is Prevotella intermedia, by F.n. is Fusobaterium nucleatum, by W.r. is Wolinella recta, by B.f. is Bacteroides forsythus, and by T.d. is Treponema denticola.

[Example 1] Toothpaste

| | |
|---|---|
| Calcium hydrogenphosphate dihydrate | 50.0% |
| Glycerine | 20.0 |
| Carboxymethylcellulose | 1.0 |
| Sodium laurylsulfate | 1.5 |
| Sodium lauroylsarcosinate | 0.5 |
| Flavor | 1.0 |
| Saccharin | 0.1 |
| Dextranase | 0.01 |
| Rabbit antiserum (Anti-A.a. surface layer polysaccharide-BSA) | 0.1 |
| Water | balance |
| Total | 100.0% |

[Example 2] Toothpaste

| | |
|---|---|
| Calcium hydrogenphosphate dihydrate | 47.0% |
| Sorbit | 10.0 |
| Glycerine | 10.0 |
| Carboxymethylcellulose | 1.0 |
| Sodium laurylsulfate | 2.0 |
| Flavor | 1.0 |
| Saccharin | 0.1 |
| Ethanol | 2.0 |
| Chlorhexadine gluconate | 0.01 |
| Mutanase | 0.1 |
| Chicken egg antibody (Anti-P.g. surface layer polysaccharide - egg albumin) | 0.1 |
| Water | balance |
| Total | 100.0% |

[Example 3] Toothpaste

| | |
|---|---|
| Calcium carbonate | 48.0% |
| Glycerine | 20.0 |
| Carrageenan | 0.5 |
| Carboxymethylcellulose | 1.0 |
| Lauryldiethanol amide | 1.0 |
| Sucrose monolaurate | 2.0 |
| Flavor | 1.0 |
| Tranexamic acid | 0.05 |
| Saccharin | 0.1 |
| Bovine anti-polysaccharide (a, b, c) milk | 0.05 |
| Water | balance |
| Total | 100.0% |

[Example 4] Toothpaste

| | |
|---|---|
| Aluminium hydroxide | 50.0% |
| Glycerine | 20.0 |
| Carboxymethylcellulose | 2.0 |
| Sodium laurylsulfate | 2.0 |
| Flavor | 1.0 |
| Saccharin | 0.1 |
| Goat antiserum (Anti-P.g. surface layer polysaccharide - BSA) | 0.1 |
| Water | balance |
| Total | 100.0% |

[Example 5] Toothpaste

| | |
|---|---|
| Silicid anhydride | 30.0% |
| Glycerine | 30.0 |
| Sorbit | 20.0 |
| Carboxymethylcellulose | 1.0 |
| Sodium laurylsulfate | 2.0 |
| Flavor | 1.0 |
| Saccharin | 0.1 |
| Sodium fluoride | 0.1 |
| Ethanol | 2.0 |
| Chicken egg anti-polysaccharide (a) antibody | 0.5 |
| Chicken egg anti-polysaccharide (b) antibody | 0.5 |
| Chicken egg anti-polysaccharide (c) antibody | 0.5 |
| Water | balance |
| Total | 100.0% |

[Example 6] Toothpowder

| | |
|---|---|
| Calcium hydrogenphosphate dihydrate | 50.0% |
| Calcium carbonate | 30.0 |
| Glycerine | 10.0 |
| α-olefin sulfonate | 1.0 |
| Flavor | 1.0 |
| Saccharin | 0.1 |
| Dextran | 0.5 |
| Horse antiserum (Anti-F.n. surface layer polysaccharide) | 0.05 |
| Water | balance |
| Total | 100.0% |

[Example 7] Liquid Dentifrice

| | |
|---|---|
| Sodium polyacrylate | 50.0% |
| Glycerine | 30.0 |
| Flavor | 0.9 |
| Saccharin | 0.1 |
| Ethanol | 3.0 |

-continued

| | |
|---|---|
| Cetylpyridinium chloride | 0.05 |
| Linolic acid | 0.05 |
| Goat anti-polysaccharide (b) - BSA milk | 0.01 |
| Water | balance |
| Total | 100.0% |

[Example 8] Mouthwash

| | |
|---|---|
| Ethanol | 20.0% |
| Flavor | 1.0 |
| Saccharin | 0.05 |
| Lauryl diethanolamide | 0.3 |
| Goat antiserum (Anti-W.r. surface layer polysaccharide) | 0.01 |
| Water | balance |
| Total | 100.0% |

[Example 9] Tablets for Gargle

| | |
|---|---|
| Sodium hydrogencarbonate | 54.0% |
| Dibasic sodium phosphate | 10.0 |
| Polyethylene glycol | 3.0 |
| Citric acid | 17.0 |
| Sodium sulfate (anhydride) | 13.6 |
| Flavor | 2.0 |
| Chlorhexidine gluconate | 0.05 |
| Oleic acid | 0.1 |
| Rabbit antiserum (Anti-B.f. surface layer polysaccharide-γ-globulin) | 0.01 |
| Water | balance |
| Total | 100.0% |

[Example 10] Massage Cream for Gingiva

| | |
|---|---|
| White veselin | 8.0% |
| Propylene glycol | 4.0 |
| Stearyl alcohol | 8.0 |
| Polyethylene glycol 4000 | 25.0 |
| Polyethylene glycol 400 | 37.0 |
| Tocopherol acetate | 0.1 |
| Sucrose stearic ester | 0.5 |
| Bovine antiserum (Anti-T.d. surface layer polysaccharide - BSA) | 0.01 |
| Water | balance |
| Total | 100.0% |

[Example 11] Chewing Gum

| | |
|---|---|
| Gum base | 43.85% |
| Calcium carbonate | 2.0 |
| Thick malt syrup | 15.0 |
| Sugar | 25.0 |
| Sucrose palmitate | 1.0 |
| Fructose | 4.0 |
| Maltose | 1.0 |
| Flavor | 1.0 |
| Chicken egg antibody (Anti-A.a. surface layer polysaccharide - BSA) | 0.01 |
| Water | balance |
| Total | 100.0% |

[Example 12] Troche

| | |
|---|---|
| Gum arabi | 6.0% |
| Glucose | 72.0 |
| Gelatin | 3.0 |
| Flavor | 0.2 |
| 1-menthol | 0.1 |
| Spearmint oil | 0.1 |
| Sodium ascorbate | 0.1 |
| Goat anti-polysaccharide (a)-casein milk | 0.01 |
| Water | balance |
| Total | 100.0% |

[Example 13] Oral Paste

| | |
|---|---|
| Polyoxyethylene monostearate | 2.0% |
| Sorbitan monostearate | 2.0 |
| Cetyl alcohol | 2.0 |

-continued

| | |
|---|---|
| Palmityl alcohol | 3.0 |
| Propylene glycol | 15.0 |
| Carboxymethylcellulose | 5.0 |
| Gelatin | 1.0 |
| Saccharin | 0.2 |
| Peppermint oil | 0.5 |
| Spearmint oil | 0.5 |
| Horse antiserum (Anti-P.i. surface layer polysaccharide) | 0.05 |
| Lyzochyme chloride | 5000 units/g |
| Water | balance |
| Total | 100.0% |

[Example 14] Oral Paste

| | |
|---|---|
| Glyceryl monolaurate | 3.0% |
| Oleyl alcohol | 5.0 |
| Polyethylene glycol | 15.0 |
| White vaselin | 3.0 |
| Monosodium N - palmitoylglutaminate | 0.5 |
| Hydroxyethyl cellulose | 5.0 |
| Tocopherol acetate | 0.1 |
| Sodium saccharin | 0.2 |
| Japanese peppermint oil | 0.7 |
| Carvone | 0.5 |
| Anethole | 0.3 |
| Eugenol | 0.1 |
| Chicken egg anti-polysaccharide (c) - ovalbumin antibody | 0.05 |
| Water | balance |
| Total | 100.0% |

[Example 15] Ice Cream

| | |
|---|---|
| Cream (fat content of 50%) | 16.84% |
| Cow's milk (fat content of 3.7%) | 42.65 |
| Evaporated defatted milk | 24.24 |
| Sugar | 11.25 |
| Corn syrup | 4.65 |
| Stabilizer | 0.35 |
| Total | 100.0% |

[Example 16] Ice Cream

| | |
|---|---|
| Cream (fat content of 40%) | 31.54% |
| Cow's milk (fat content of 3.7%)** | 37.16 |
| Evaporated defatted milk | 15.08 |
| Sugar | 11.25 |
| Corn syrup | 4.67 |
| Stabilizer | 0.30 |
| Total | 100.0% |

[Example 17] Yogurt

| | |
|---|---|
| Defatted milk | 320 kg |
| Sweetened condensed milk*** | 56 |
| Sugar | 23 |

The above ingredients are fermented according to a conventional process.

[Example 18] Bavarian Cream

| | |
|---|---|
| Cow's milk**** | 375 cc |
| Sugar | 60 g |
| Vagina of vanilla | one piece |
| Yolk | five |
| Gelatin | 20 g |
| Fresh cream | 75 cc |

*The milk contains 0.5% of bovine anti-polysaccharide (a, b, c) milk.
**The milk contains 5% of bovine anti-P.g. surface layer polysaccharide-BSA milk.
***The milk contains 10% of bovine anti-A.a. surface layer polysaccharide-BSA milk.
****The milk contains 5% of bovine anti-P.g. surface layer polysaccharide milk.

What is claimed is:

1. An oral composition in the form of a dentifrice, which comprises an antibody obtained by immunizing an animal with an antigen that consists of at least one polysaccharide derived from the surface layer of *Actinobacillus actinomyce-* temcomitans or *Porphyromonas gingivalis*, and a pharmaceutically acceptable carrier.

2. The oral composition according to claim 1, wherein said antibody is present in said composition in an amount of from 0.0002 to 10 wt % of said composition.

3. An oral composition in the form of a dentifrice, which comprises an antibody obtained by immunizing an animal with an antigen conjugated with a polypeptide that can increase antibody titer in a mammal with respect to a polysaccharide when conjugated with said polysaccharide, wherein said antigen consists of at least one polysaccharide derived from the surface layer of *Actinobacillus actinomycetemcomitans* or *Porphyromonas gingivalis*, and a pharmaceutically acceptable carrier.

4. The oral composition according to claim 3, wherein said antibody is present in said composition in an amount of from 0.0002 to 10 wt % of said composition.

5. An oral composition in the form of a dentifrice, which comprises an antibody obtained by immunizing an animal with an antigen consisting of at least one polysaccharide selected from the group consisting of polysaccharides of formulas (a), (b), and (c):

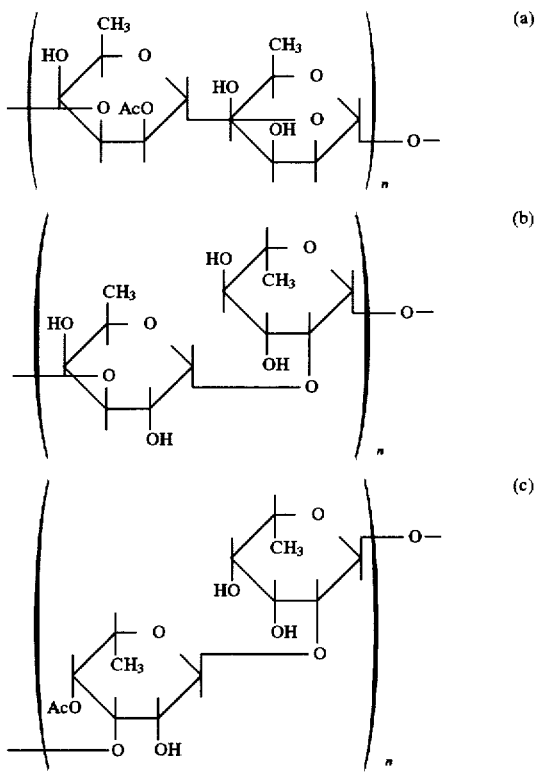

wherein Ac represents an acetyl group and n is an integer of from 1 to 1,000, and a pharmaceutically acceptable carrier.

6. The oral composition according to claim 5, wherein said antibody is present in an amount from 0.0002 to 10 wt % of said composition.

7. An oral composition in the form of a dentifrice, which comprises an antibody obtained by immunizing an animal with an antigen-polypeptide conjugate, wherein said antigen consists of the polysaccharide of formula (b):

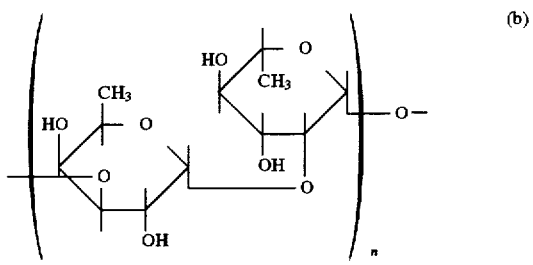

wherein n is an integer of from 1 to 1,000, and wherein said polypeptide increases antibody titer with respect to said polysaccharide antigen (b), and a pharmaceutically acceptable carrier.

8. The oral composition according to claim 7, wherein said polypeptide is a member selected from the group consisting of an albumin, γ-globulin, casein, biotin, choleratoxin B subunit, ferritin, transferrin, cytochrome C, and myosin.

9. The oral composition according to claim 8, wherein said albumin is selected from the group consisting of bovine serum albumin and ovalbumin.

10. The oral composition according to claim 6, wherein said antibody is present in an amount from 0.002 to 5 wt % of said composition.

11. The oral composition according to claim 5, wherein said composition is in a form selected from the group consisting of toothpaste, toothpowder, and a liquid dentifrice.

12. A method of suppressing colonization of periodontal disease-associated bacteria on oral surfaces, comprising administering to a subject a therapeutically effective amount of the skid oral composition of claim 5.

13. The method of claim 12, wherein said antibody is administered in a dose of from 0.0001 to 50 mg/kg/day.

14. The oral composition according to claim 5, wherein said antigen consists of said polysaccharide of formula (a).

15. The oral composition according to claim 5, wherein said antigen consists of said polysaccharide of formula (b).

16. The oral composition according to claim 5, wherein said antigen consists of said polysaccharide of formula (c).

17. The oral composition according to claim 5, wherein said antigen consists of a mixture of said polysaccharides of said formulas (a), (b), and (c).

18. The method according to claim 12, wherein said antigen consists of said polysaccharide of formula (b).

19. The method according to claim 18, wherein said antibody is administered in a dose of from 0.0001 to 50 mg/kg/day.

* * * * *